United States Patent [19]

Gueremy et al.

[11] Patent Number: 4,882,345

[45] Date of Patent: Nov. 21, 1989

[54] USE OF A COMPOUND FOR THE TREATMENT OF SCHIZOPHRENIA

[75] Inventors: Claude Gueremy, Houilles; Françoise Maillard, La Celle Saint Cloud; Bruno Musch, Paris, all of France

[73] Assignee: Rhone-Poulenc Sante, Antony, France

[21] Appl. No.: 234,602

[22] Filed: Aug. 22, 1988

[30] Foreign Application Priority Data

Aug. 25, 1987 [FR] France ............................ 87 11882

[51] Int. Cl.$^4$ .......................................... A61K 31/425
[52] U.S. Cl. ................................................ 514/367
[58] Field of Search .................................... 514/367

[56] References Cited

U.S. PATENT DOCUMENTS 4,370,338 1/1983 Mizoule .............................. 514/270

FOREIGN PATENT DOCUMENTS 0050551 of 0000 .

OTHER PUBLICATIONS

Arthur Rifkin, Drug Treatment of Acute Schizophrenia, 1095-1099.
John M. Kane, Maintenance Pharmacotherapy in Schizophrenia, 1103-1109.
Goodman and Gilman's, The Pharmacological Basis of Therapeutics Cover Sheet.
Ross J. Baldessarini, Drugs and the Treatment of Psychiactric Disorders 387.
Stewart C. Harvey, Hypnotics and Sedatives, 339-340.
Nancy C. Andreasen, Negative Symptoms in Schizophrenia 744-788.
William T. Carpenter, Jr. Deficit and Nondeficit Forms of Schizophrenia: The Concept.

*Primary Examiner*—Stanley J. Friedman
*Attorney, Agent, or Firm*—Stevens, Davis, Miller & Mosher

[57] ABSTRACT

2-amino-6-(trifluoromethoxy)benzothiazole or a pharmaceutically accpetable salt thereof is useful for the treatment of schizophrenia, particularly the negative forms thereof.

4 Claims, No Drawings

USE OF A COMPOUND FOR THE TREATMENT OF SCHIZOPHRENIA

The present invention relates to the application of 2-amino-6-(trifluoromethoxy)benzothiazole or a pharmaceutically acceptable salt thereof for obtaining a medicinal product intended for the treatment of schizophrenia, and more especially its negative forms.

It is known from European Pat. No. 50,551 that 2-amino-6-(trifluoromethoxy)benzothiazole is useful as an anticonvulsant, anxiolytic and hypnotic medicinal product.

It has now been found that 2-amino-6-(trifluoromethoxy)benzothiazole or a pharmaceutically acceptable salt thereof is useful in the treatment of schizophrenia, and more especially the negative forms of schizophrenia.

This new therapeutic application was determined in man in strict single-drug therapy. 26 schizophrenic patients were treated at a dose of 150 mg per day orally for 28 days.

The efficacy of this compound was determined according to the following scales of assessment:

SANS (ANDREASEN's scale of assessment of negative symptoms), N. C. ANDREASEN, Arch. Gen. Psychiatry vol. 39, 784–788 (1982);

BPRS (Brief Psychiatric Rating Scale), P. PICHOT et al., Revue de Psychologie Appliquee vol. 19, No. 3, 217–232 (1969);

Hamilton Anxiety Scale, P. BECH et al., Acta Psychiatrica Scandinavica supplementum No. 326, vol. 73, p. 9, 19–22, 1986;

CGI (Clinical Global Impression), ECDEU assessment manual, US Department of Health, Education and Welfare, p. 218–221.

The main symptoms improved are:
resumption of contact with the surroundings,
patient more lively, from both the kinetic and the mental standpoint,
resocialisation,
improvement in sleep.

No clinical side effect was observed.

2-Amino-6-(trifluoromethoxy)benzothiazole may be prepared according to the process described in Patent EP 50,551.

The medicinal products which are useful in the treatment of schizophrenia consist of 2-amino-6-(trifluoromethoxy)benzothiazole or a pharmaceutically salt thereof either alone or in the form of a composition in which it is combined with any other pharmaceutically compatible product, which may be inert or physiologically active. These medicinal products may be used orally, parenterally or rectally.

As solid compositions for oral administration, tablets, pills, powders (gelatin capsules, wafer tablets) or granules may be used. In these compositions, the active principle is mixed with one or more inert diluents such as starch, cellulose, sucrose, lactose or silica. These compositions can also comprise substances other than diluents, e.g. one or more lubricants such as magnesium stearate or talc, a colouring, a coating (dragées) or a lacquer.

As liquid compositions for oral administration, there may be used solutions, suspensions, emulsions, syrups and elixirs which are pharmaceutically acceptable, containing inert diluents such as water, ethanol, glycerol, vegetable oils or liquid paraffin. These compositions can comprise substances other than diluents, e.g. wetting, sweetening, thickening, flavouring or stabilizing products.

The compositions for parenteral administration may be sterile suspensions, emulsions or nonaqueous solutions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization can be carried out in several ways, e.g. by aseptic filtration, by incorporating sterilizing agents in the composition, by irradiation or by heating. The compositions can also be prepared in the form of sterile solid compositions which can be dissolved in an injectable sterile medium immediately prior to administration.

The compositions for rectal administration may be suppositories or rectal capsules containing, apart from the active product, excipients such as cocoa butter, semi-synthetic glycerides or polyethylene glycols.

The doses depend on the effect desired, on the length of the treatment and on the administration route used; they are generally between 50 and 500 mg orally per day for an adult, with unit doses ranging from 10 to 50 mg of active substance.

Generally speaking, the doctor will determine the appropriate dosage in accordance with the age, weight and all other factors specific to the subject to be treated.

The examples which follow illustrate pharmaceutical compositions which are usable for the treatment of schizophrenia.

EXAMPLE A

Gelatin capsules containing a 50-mg dose of active product and having the following composition are prepared according to the usual technique:
2-amino-6-(trifluoromethoxy)benzothiazole: 50 mg
cellulose: 18 mg
lactose: 55 mg
colloidal silica: 1 mg
sodium carboxymethyl starch: 10 mg
talc: 10 mg
magnesium stearate: 1 mg

EXAMPLE B

Tablets containing a 50-mg dose of active product and having the following composition are prepared according to the usual technique:
2-amino-6-(trifluoromethoxy)benzothiazole: 50 mg
Lactose: 104 mg
cellulose: 40 mg
polyvidone: 10 mg
sodium carboxymethylstarch: 22 mg
Talc: 10 mg
Magnesium stearate: 2 mg
Colloidal silica: 2 mg
Mixture of hydroxymethylcellulose, glycerin and titanium oxide (72:3.5:24.5): qs 1 finished film-coated tablet weighing 245 mg

EXAMPLE C

An injectable solution is prepared containing 10 mg of active product and having the following composition:
2-amino-6-((trifluoromethoxy)benzothiazole: 10 mg
benzoic acid: 80 mg benzyl alcohol: 0.06 cc
sodium benzoate: 80 mg
ethanol, 95% strength: 0.4 cc
sodium hydroxide: 24 mg
propylene glycol: 1.6 cc
water: qs 4 cc

We claim:

1. Method of treatment of schizophrenia comprising administering to a subject suffering therefrom or liable thereto an effective amount of 2-amino-6-(trifluoromethoxy)-benzothiazole or pharmaceutically acceptable salt thereof.

2. Method of treatment of a negative form of schizophrenia comprising administering to a subject suffering therefrom or liable thereto an effective amount of 2-amino-6-(trifluoromethoxy)benzothiazole or pharmaceutically acceptable salt thereof.

3. Method of treatment according to claim 1 in which the 2-amino-6-(trifluoromethoxy)benzothiazole or pharmaceutically acceptable salt thereof is administered orally, parenterally or rectally.

4. Method of treatment according to claim 2 in which the 2-amino-6-(trifluoromethoxy)benzothiazole or pharmaceutically acceptable salt thereof is administered orally, parenterally or rectally.

* * * * *